United States Patent [19]

Lam

[11] 4,119,405

[45] Oct. 10, 1978

[54] TEST MEANS AND METHOD FOR INTERFERENCE RESISTANT DETERMINATION OF OXIDIZING SUBSTANCES

[75] Inventor: Charles Tak Wai Lam, Elkhart, Ind.

[73] Assignee: Miles Laboratories, Inc., Elkhart, Ind.

[21] Appl. No.: 877,499

[22] Filed: Feb. 13, 1978

[51] Int. Cl.$^2$ .................. G01N 33/16; C12K 1/04; C12K 1/10

[52] U.S. Cl. .................. 422/56; 23/230 R; 23/230 B; 195/103.5 R; 252/408

[58] Field of Search .......... 23/230 R, 230 B, 253 TP; 252/408; 195/103.5 R

[56] References Cited

U.S. PATENT DOCUMENTS 3,979,262   9/1976   Hunziker .................. 195/103.5 R

OTHER PUBLICATIONS

Gochman et al., "Automated Determination of Uric Acid with use of a Uricase-Peroxide System" Chin. Chem., vol. 17, No. 12, pp. 1154-1159, (1971).

Primary Examiner—R.E. Serwin
Attorney, Agent, or Firm—Charles J. Herron

[57] ABSTRACT

Test means, such as a composition or device, method of making a test device and process for determination of at least one oxidizing substance, such as a peroxide, are disclosed. More particularly, the contemplated test means comprises a hydrazone and a hydroxynapthalenesulfonate selected from the group 4,5-dihydroxy-2,7-naphthalene disulfonic acid (chromotropic acid) and 1-hydroxy-2-naphthalene sulfonic acid. Further provided is a test system for the determination of a constituent in a sample, having means responsive to the presence of said constituent in said sample to produce at least one oxidizing substance and a composition for determining said at least one oxidizing substance, having the improvement wherein said composition comprises a hydrazone and a hydroxynapthalenesulfonate selected from the group of 4,5-dihydroxy-2,7-naphthalene disulfonic acid and 1-hydroxy-2-naphthalene sulfonic acid. The test system is preferably of the type which determines peroxides formed from enzymatic conversion of constituents in biological fluids. When in the form of compositions the test means can optionally be incorporated with a carrier, such as a tablet or matrix, to provide a test device. The indicator system is highly sensitive to low levels of body fluid constituents to be detected while also being highly resistant to interfering reducing substances, such as ascorbic acid, often present in body fluids.

24 Claims, 5 Drawing Figures

TEST MEANS AND METHOD FOR INTERFERENCE RESISTANT DETERMINATION OF OXIDIZING SUBSTANCES

BACKGROUND OF THE INVENTION

The present invention relates generally to the field of diagnostic tests and, more particularly, to those tests useful in qualitative and quanitative determination of biological components, such as glucose and uric acid, in which tests such components are converted to an oxidizing substance, such as a peroxide.

Glucose oxidase enzymatically converts glucose to gluconic acid and hydrogen peroxide. The hydrogen peroxide thus formed can be reduced to $H_2O$ by a peroxidatively active substance in the presence of an indicator system which is oxidized to produce a response, such as a color change. The chromogenic indicator o-tolidine has been used for some time in glucose test systems, but provides results which are subject to reduction of the oxidized indicator by interfering substances, such as ascorbic acid. Further, the safety of o-tolidine has been questioned.

Likewise, uricase enzymatically converts uric acid to allantoin and hydrogen peroxide. The hydrogen peroxide formed can be reduced to $H_2O$ by a peroxidatively active substance in the presence of an indicator system, historically o-dianisidine.

More recently, Gochman and Schmitz have reported using 3-methyl-2-benzothiazolinone hydrazone hydrochloride with N,N-dimethylaniline to form an azo dye indicator in determinations of uric acid, Clin. Chem. 17:1154 (1971), and glucose Clin. Chem. 18:943 (1972). Even though it is asserted that the mixture with N,N-dimethylaniline was more resistant than o-tolidine, susceptibility to ascorbic acid interference produced significant error in reported uric acid and glucose concentrations.

The mechanism of oxidatively coupling heterocyclic hydrazones with phenols, aromatic amines and other compounds which can take part in the classic azo coupling reaction is reviewed briefly in Zollinger, Azo and Diazo Chemistry, Interscience, New York, p. 215–217 (1961). A summary of the original work, directed to the formation of azo dyes by oxidative coupling, of Hunig and co-workers in Germany (1957-68) is incorporated in Baer, Cationic Dyes for Synthetic Fibers, Venkataraman (ed.), The Chemistry of Synthetic Dyes, Vol. 4, Academic Press, N.Y., pgs. 188–193 (1971).

Hunziker, U.S. Pat. No. 3,979,262, adds a buffer, of citric or maleic acid, to the mixture of Gochman, supra, and discloses that, along with N,N-dimethylaniline, other aromatic amines can be used so long as they are not substituted in both the ortho and para positions. The buffer is also critical and maintains a predetermined pH range of from 3.2 to 4.7 for a uric acid determination and from 4.7 to 5.5 for a glucose or cholesterol determination.

The prior art, insofar as it teaches the use of hydrazone indicators in analysis for $H_2O_2$, suggests that the reaction between MBTH and dimethylaniline is resistant to the effects of reducing substances in a sample. While this may be true relative to indicators such as o-tolidine, the use of such hydrazone indicators provides very poor indications in the presence of ascorbate.

Therefore, efforts by these prior workers have failed to provide an indicator system which is either substantially free of susceptibility to the effects of interfering substances or makes use of indicators recognized for their safety.

OBJECTS OF THE INVENTION

It is therefore an object of the present invention to provide an improved test for the detection of oxidizing substances in body fluids.

It is another object of the invention to provide an improved test for those oxidizing substances which are enzymatically converted from other clinically significant body fluid components.

It is yet another object of the invention to provide an improved test for such body fluid components using materials which are recognized for their safety.

A further object of the invention is to provide an improved test for the detection of oxidizing substances in body fluids which is highly resistant to interfering reducing substances.

A still further object of the invention is to provide an improved test for the detection of oxidizing substances wherein the above-identified advantages are achieved through a novel indicator system comprising a hydrazone and a hydroxynapthalenesulfonate selected from the group of 4,5-dihydroxy-2,7-napthalene disulfonic acid (chromotropic acid) and 1-hydroxy-2-napthalene sulfonic acid.

Other objects and a fuller understanding of the invention will be had by referring to the following description and claims drawn to preferred embodiments thereof, taken in conjunction with the accompanying drawings in which:

SUMMARY OF THE INVENTION

In accordance with the present invention there are provided test means, such as a composition and device, a method of making the test device, and a process for determination of at least one oxidizing substance, such as a peroxide. More particularly, the contemplated test means comprises a hydrazone and a hydroxynapthalenesulfonate selected from the group of 4,5-dihydroxy-2,7-napthalene disulfonic acid (chromotropic acid) and 1-hydroxy-2-napthalene sulfonic acid. Further provided is a test system for the determination of a constituent in a sample, having means responsive to the presence of said constituent in said sample to produce at least one oxidizing substance and a composition for determining said at least one oxidizing substance, having the improvement wherein said composition comprises a hydrazone and a hydroxynapthalenesulfonate selected from the group of 4,5-dihydroxy-2,7-napthalene disulfonic acid and 1-hydroxy-2-napthalene sulfonic acid. The test system is preferably of the type which determines peroxides formed from enzymatic conversion of constituents in biological fluids. When in the form of a composition the test means can optionally be incorporated with a carrier, such as a tablet or matrix, to provide a test device. The indicator system is highly sensitive to low levels of body fluid constituents to be detected while also being highly resistant to interfering reducing substances, such as ascorbic acid, often present in body fluids.

In the test system, the means responsive to the presence of the consitituent in the sample to produce at least one oxidizing substance can include glucose oxidase, for glucose determination, or uricase, for uric acid determination and a peroxidatively active substance. Typical of such peroxidatively active substances are peroxidase or hemoglobin, used when hydrogen peroxide is the oxidizing substance.

Coupling is believed to occur through a mechanism such as that illustrated for 3-methyl-2-benzothiazolinone hydrazone (MBTH) and chromotropic acid (CTA) in Diagram A although this is not a theory on which the invention must be based.

Diagram A

In contrast to prior art compositions, that of the present invention is highly sensitive to low levels of body fluid constituents to be detected while also being highly resistant to the effects of competitive reducing substances, particularly ascorbic acid in urine. Since a characteristic color reaction takes place depending on the concentration of the oxidizing substance detected, quantitative detection for such body fluid components as glucose and uric acid is possible.

It is now possible by using the test composition and device of the invention to obtain interference-free detection of glucose in amounts at least as low as 1.0 milligram (mg)/deciliter (dl), even in the presence of a small but detectable amount of ascorbate, and to detect the presence of severely elevated glucose levels, over 500 mg/dl, in the presence of at least 1000 mg/dl of ascorbic acid.

DESCRIPTION OF THE PREFERRED EMBODIMENTS

Although specific terms are used in the following description for the sake of clarity, these terms are intended to refer only to the particular embodiment of the invention selected for exemplary illustration, and are not intended to define or limit the scope of the invention.

The test means according to the invention can take many physical forms and include many specific hydrazones for coupling with the contemplated hydroxynapthalenesulfonates, regardless of the form assumed. These, along with reagents, such as stabilizing agents, which can additionally be employed, if desired, are described. The test means can be used in both liquid and solid form, as can the test system, incorporating a composition of the test means as exemplified by the procedures and embodiments described below.

The hydroxynapthalenesulfonate coupling agent of the test means is preferably chromotropic acid. Another hydroxynapthalenesulfonate which is advantageously employed is 1-hydroxy-2-napthalene sulfonic acid.

The hydrazones useful in the test means are condensation products of a hydrazine with an aldehyde or ketone and contain the grouping $>C=NNH_2$. Many hydrazones are capable of oxidatively coupling with hydroxynapthalensulfonates to form a colored entity. Such include, among others, 3-methyl-2-benzothiazolinone hydrazone, 1-methyl-2-quinolinone hydrazone, N-methyl-pyridone-4-hydrazone, N-methyl-pyridone-2-hydrazone, N-methyl-quinolinone-2-hydrazone, 1-methyl-quinolinone-4-hydrazone, N-methyl-2-benzothiazolinone hydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone and 1,3-dimethyl-benzimidazolinone-2-hydrazone. In a preferred embodiment of the composition, a 3-($C_1$-$C_4$ alkyl)-2-benzothiazolinone hydrazone chromogen, such as 3-methyl-2-benzothiazolinone hydrazone (MBTH), is used. Such hydrazones are strong reducing agents.

The acid addition salts of the hydrazones can also be used. Any conventional acid addition salt can be utilized such as those formed from hydrochloric acid, hydrobromic acid, sulfuric acid, nitric acid and the like. These acid addition salts can either be used alone or they can be used in conjunction with the corresponding hydrazone.

Molar ratios of hydrazone/coupler range from about 17:1 to about 1:17, with more nearly equimolar ratios being preferred for the optimum combination of detection sensitivity and interference resistance.

The composition can further include stabilizing agents, carboxymethylcellulose and polyoxyethylene ethers of fatty alcohols (BRIJ ® made by ICI United States Inc., Wilmington, Delaware 19897) being advantageously selected.

Test means according to the invention, and test systems employing compositions of said test means, are preferably used in a generally neutral or slightly alkaline pH range, although they remain operative even at somewhat lower pH. The maintenance of a generally neutral or alkaline pH provides improved reactivity in terms of speed and resistance to interference in contrast to the teaching of the prior art.

The test system comprises, along with the composition according to the invention, means responsive to the presence of a constituent to be determined in a sample to produce an oxidizing substance for determination by the composition. Such means are preferably enzymatic in nature. For example, when glucose is to be determined, glucose oxidase and peroxidase are used to form $H_2O_2$ therefrom. Likewise, when uric acid is to be determined, uricase and peroxidase comprise the constituent-responsive means. The concentrations and types of reagents useful in the constituent-responsive means are contemplated to include those known to the art.

The test means can be used as a solution for determination of oxidative substance in a sample. Further, the test system for determination of constituents converted to such oxidative substances, containing the test means in composition form, can be used as a solution. The test system is preferably used to detect biological, such as body fluid, constituents by adding it to a specimen such as urine, serum, cerebrospinal fluid, tissue culture supernatant or the like. For assays using the test system in liquid form, the peroxidase should be segregated from the other reagents until ready for use. The determination is allowed to go forward by introduction of the segregated reagent, such as the peroxidase.

When used in solution, whether in the test means itself or as a composition thereof in a test system, the hydroxynapthalenesulfonate according to the invention is preferably used in concentrations of from about $10^{-5}$ Molar (M) to about $10^{-3}$ M. Likewise, the hydrazone is preferably used in concentrations of from about $10^{-5}$ M to about $10^{-3}$ M. When one or more stabilizing agents are included, they are preferably present in total concentrations of from about 0.5 mg/deciliter (dl) to about 5.0 mg/dl. When peroxidase is at least one of the reagents comprising the constituent-responsive means of the test system, concentrations of the peroxidase are preferably from about 10 µg (micrograms)/l to about 200 µg/l. The solvent used in preparing the solutions can be water, physiological solutions, organic solvents, such as methanol, or mixtures thereof.

Also provided are test devices incorporating the test means or the test system of the invention and a method of making such reagent test devices which comprises incorporating a carrier, such as a matrix or tablet, with the test means or test system, respectively. When this incorporation is by impregnation with a solution of the composition according to the invention, including a test system, the carrier so impregnated is then dried. In addition to impregnation, the devices of the present invention can be made by other suitable techniques such as printing or spraying the composition onto a substrate or matrix.

The device is preferably prepared by a multi-dip process. The concentrations of reagents used in the dips range from about $10^{-3}$ M up to a saturated solution. Most generally useful for the hydrazone and coupler is a concentration of about 0.02 M each. Peroxidase concentration is from about 0.015 mg/ml to about 2 mg/ml of dip solution.

Solid preparations are preferably incorporated with a carrier matrix in strip format. The term carrier matrix can be envisioned to refer to bibulous and non-bibulous matrices which are insoluble in and maintain their structural integrity when exposed to water or physiological fluids. Suitable bibulous matrices which can be used include paper, cellulose, wood, synthetic resin fleeces, glass fiber, woven and non-woven fabrics and the like. Non-bibulous matrices include organo-plastic materials such as polypropylene or the like. When a bibulous matrix is employed, the matrix is advantageously affixed by suitable means, such as double-faced adhesive tape, to an insoluble support member, such as an organo-plastic strip, e.g. polystyrene, for ease of use.

Alternatively, the compositions of the invention can be embodied in a carrier taking the form of a pressed or molded tablet containing conventional carrier material.

The test device is advantageously used by momentarily dipping it in a test sample or by otherwise introducing a test sample into the carrier matrix, whereby a detectable color change results when oxidative components are present. The test device can be used in the same way when samples of plasma, serum or other body fluids are tested.

The relationship between K (the absorption coefficient of the specimen), reported in some of the examples, and the concentration of absorbing species (such as uric acid or glucose) is given by the Kubelka-Monk equation which is provided, along with a detailed discussion of reflectance spectrophotometry in Kortumi, G., *Reflectance Spectroscopy*, Springer-Verlag Inc., New York, 1969. K is defined as twice the absorbance/unit path length (2A/b) in transmission measurements. In work here it is assumed to be proportional to the concentration of colored indicator molecules formed. In the relationship defined by the Kubelka-Monk equation the percent reflectance (%R) value decreases as the concentration of oxidative substance detected increases, and vice versa. Thus, the readings taken inversely correlate, according to the equation, with the concentration of absorbing species detected. Readings were taken at the wavelengths indicated.

Reflectance readings can be obtained from commercially available spectrophotometers such as Beckman DK-2 Spectrophotometer, Beckman Instruments, Inc., Fullerton, California 92634 or Spectrocolorimeter SCF-1, Israel Electro-Optical Industry Ltd. (distributed in the U.S. by Broomer Research Corporation, Plainwell, Long Island, N.Y. 11803).

Horseradish peroxidase and glucose oxidase were obtained from Miles Research Products, Miles Laboratories, Elkhart, Indiana 46515. A copolymer of methyl vinyl ether and maleic anhydride (Gantrez AN-139) and polyvinyl pyrrolidine (PVP) were obtained from GAF Corp., Chemical Products, N.Y., N.Y. 10020). The 3-methyl-2-benzothiazolinone hydrazone hydrochloride monohydrate (MBTH), other hydrazones, chromotropic acid, 4,5-dihydroxy-2,7-naphthalene disulfonic acid disodium salt dihydrate, 1-hydroxy-2-napthalene sulfonic acid, 1-hydroxy-3-napthalene sulfonic acid, 1-hydroxy-5-napthalene sulfonic acid, 3-dimethylaminobenzoic acid, 3-dimethylaminobenzoic acid, and violet acid (1-naphthol-3,6-disulfonic acid) were obtained from Aldrich Chemical Co., Inc., Milwaukee, Wisconsin 53233. Standard reagent grade solvents and reagents were used.

The examples shown are merely illustrative and are not to be construed as a limitation of the invention. One skilled in the art will be able to make such variations, substitutions and changes in the ingredients and parameters as may seen desirable.

EXAMPLE I

Test devices incorporating compositions according to the invention were prepared and compared for sensitivity in the detection of glucose with commercially available devices which use prior art indicators.

The first impregnating solution was prepared in 42.5 milliliters (ml) distilled $H_2O$ to which the following was added, with stirring:

| citric acid | 714 milligrams (mg) |
|---|---|
| sodium citrate | 3136 mg |
| $Na_4EDTA$ (sodium salt of ethylene diamine tetraacetic acid) | 2400 mg |
| glucose oxidase (5000 I.U. per ml) | 15 ml |
| peroxidase (100 I.U. per mg) | 324 mg |
| polyvinyl pyrrolidine (PVP) | 360 mg/3.6 ml $H_2O$ |
| Gantrez AN-139 | 720 mg/14.4 ml |

An International Unit (I.U.) of enzyme activity is effective to catalyze the conversion of 1 micromole ($\mu$mole) of substrate per minute under specified conditions of pH and temperature. Sheets of Whatman 3MM filter paper (Whatman, Inc., Clifton, N.J. 07014) were impregnated to saturation with the above-prepared solution and dried at 87° Centrigrade (C.).

A second impregnating solution was prepared in 50 ml of a 4:1 methanol/$H_2O$ solvent to which the following were added, with stirring:

MBTH; 0.02 grams (g.)
chromotropic acid; 0.05 g.
sodium lauryl sulfate; 0.20 g.

The above-prepared paper, containing the dried residue of the first impregnating solution, was then impregnated to saturation with the second impregnating solution and dried at 60° C. The paper so prepared was cut to 2.5 millimeters (mm) × 2.5 mm to form devices according to the invention, identified in this Example as MBTH/CTA. The devices were then backed with double-faced adhesive tape and fixed thereby to organoplastic support members.

The devices prepared according to the invention were compared to CLINISTIX ® reagent strips (o-tolidine), DIASTIX ® reagent strips (potassium iodide) and S-GLUKOTEST ® (o-tolidine). CLINISTIX ® and DIASTIX ® are registered trademarks for products of Ames Company, Division of Miles Laboratories, Inc., Elkhart, Indiana 46515 and S-GLUKOTEST ® is available from Biodynamics/BMC, Indianapolis, Indiana. All devices were tested by momentarily immersing them in urine solutions of known glucose concentration. Color development in each was used in an attempt to differentiate between 0, 1, 2, 5, 10, 20, 30, 50 and 100 milligrams/deciliter (mg/dl). A reported reading of "0" indicated no detectable response, while "50" indicated detection of at least 50 mg/dl in the sample. Intermediate numbers indicate relative, visibly distinguishable, color intensity as observed. The results are shown in Table 1.

Table 1

| Glucose (mg/%) | CLINISTIX ® | DIASTIX ® | S-GLUKOTEST ® | MBTH/CTA |
|---|---|---|---|---|
| 0 | 0 | 0 | 0 | 0 |
| 1 | 0 | 0 | 0 | 5 |
| 2 | 0 | 0 | 0 | 10 |
| 5 | 0 | 0 | 0 | 20 |
| 10 | 0 | 0 | 0 | 30 |
| 20 | 0 | 0 | 0 | 38 |
| 30 | 0 | 1 | 0 | 42 |
| 50 | 5 | 8 | 8 | 50 |
| 100 | 10 | 10 | 10 | 50 |

The results shown above indicate that devices prepared with test compositions according to the present invention are sensitive to levels of glucose much lower than those which were detectable by prior art devices.

EXAMPLE II

In the experiments described in this example, the relative ascorbate resistance of various MBTH-coupler systems was compared to each other and to o-tolidine.

A first impregnating solution was prepared to contain the following:

| Distilled Water | 40 ml. |
|---|---|
| Ethanol | 40 ml. |
| Gantrez AN 139 5% weight/volume (w/v) in distilled water | 52 ml. |
| Tris malonate buffer [2.8 M Tris (hydroxymethyl)aminomethane; 1.4 M malonic acid; 1.4 M sodium malonate] | 32 ml. |
| Polyvinyl pyrrolidone 10% w/v in distilled water | 28 ml. |
| 200 mg Peroxidase in 4.3 ml glucose oxidase (1000 v/ml) + 19.3 ml distilled water | |

Sheets of Eaton-Dikeman 204 filter paper (E&D) were impregnated to saturation with the above-prepared solution and dried at 60° C.

A first portion of these dried papers was saturated with 0.02 M o-tolidine in $CHCl_3$ and dried at 50° C. to form the o-tolidine devices used. The remaining or second portion of the above-prepared dried papers was then impregnated to saturation with a solution of 50 ml of methanol having 234 mg MBTH hydrochloride monohydrate dissolved therein, and dried at 60° C.

In a third impregnation, the paper sheets of the second portion above were each impregnated to saturation with the indicated solution of one of the following potential couplers:

| Chromotropic Acid | 400 mg in 40 ml methanol + 10 ml water |
|---|---|
| Violet Acid | 350 mg in 40 ml methanol + 10 ml water |
| Dimethylaminobenzoic Acid | 165 mg in 50 ml methanol |
| Diethylaniline | 186 mg in 50 ml methanol |

The papers so impregnated were then dried at 60° C. to form devices.

These devices were tested with 100 mg/dl urine glucose solutions containing either 0 or 50 mg/dl ascorbate and any color changes were read by the use of a recording reflectance spectrophotometer. Reflectance values at specific wavelengths were converted, by the Kubelka-Monk equation described previously, to equivalent absorbance values (K) and plotted as a function of time.

In assessing relative ascorbate resistance, data for the first 30 seconds were used, as there was a generally linear response of K with time during that period. This is graphically illustrated by the sample plots shown in FIGS. 1-3. A ratio of slopes was used in which the slope of K vs. time for data taken in the presence of 50 mg/dl ascorbate was divided by the slope of K vs. time for data taken in the absence of ascorbate. A value of 1 would mean no ascorbate interference; a value of 0 would mean complete ascorbate interference. Results are shown in Table 2.

Table 2
RELATIVE ASCORBATE INTERFERENCE

| Indicator | λ Observed (nM) | Slope at 50 mg/dl Ascorbate / Slope at 0 Ascorbate |
|---|---|---|
| o-Tolidine | 610 | 0.005 |
| MBTH - Chromotropic Acid (CTA) | 560 | 0.42 |
| MBTH - Violet Acid | 540 | 0.08 |
| MBTH - Dimethylaminobenzoic Acid | 600 | 0.08 |
| MBTH - Diethylaniline (DEA) | 600 | 0.07 |

Figure 1:
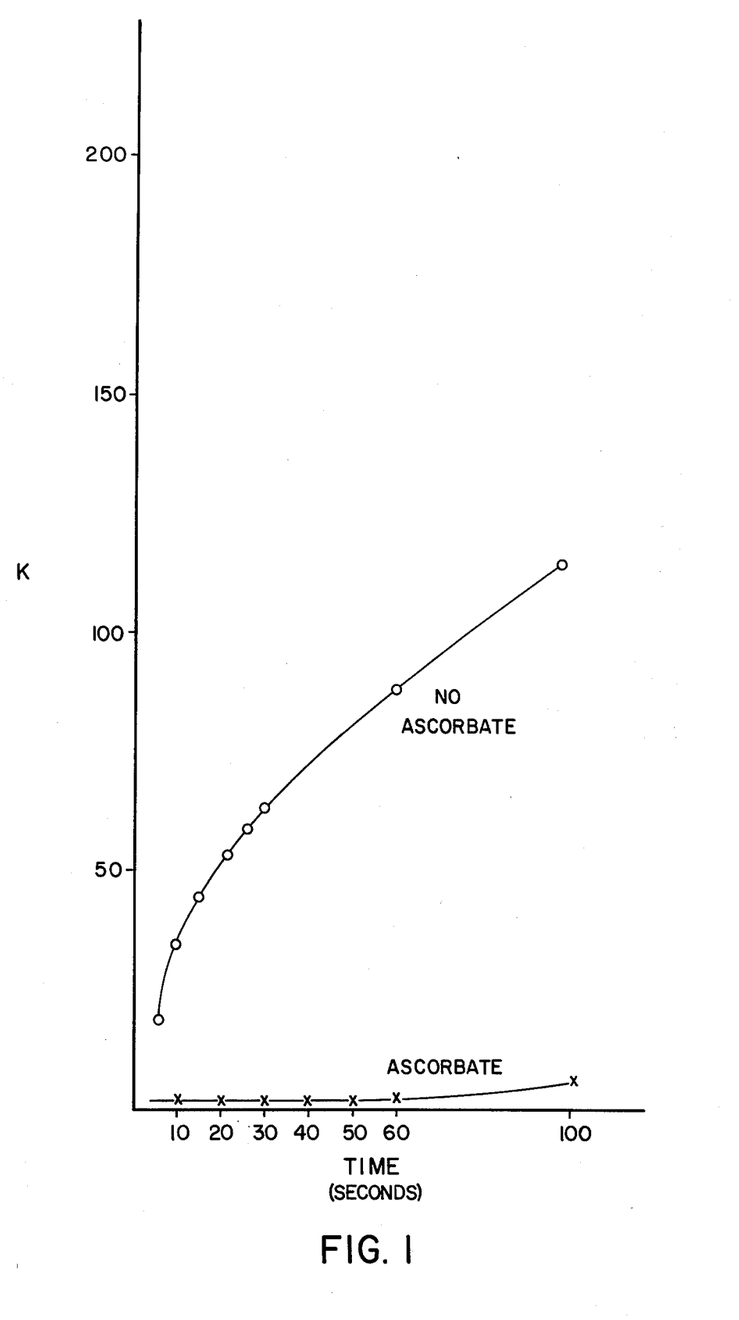
FIG. 1 is a graphical representation of the data reported in Example II for a glucose oxidase-peroxidase reagent test using o-tolidine as the indicator, obtained by plotting the absorption coefficient of the specimen (K) vs. time.
Figure 2:
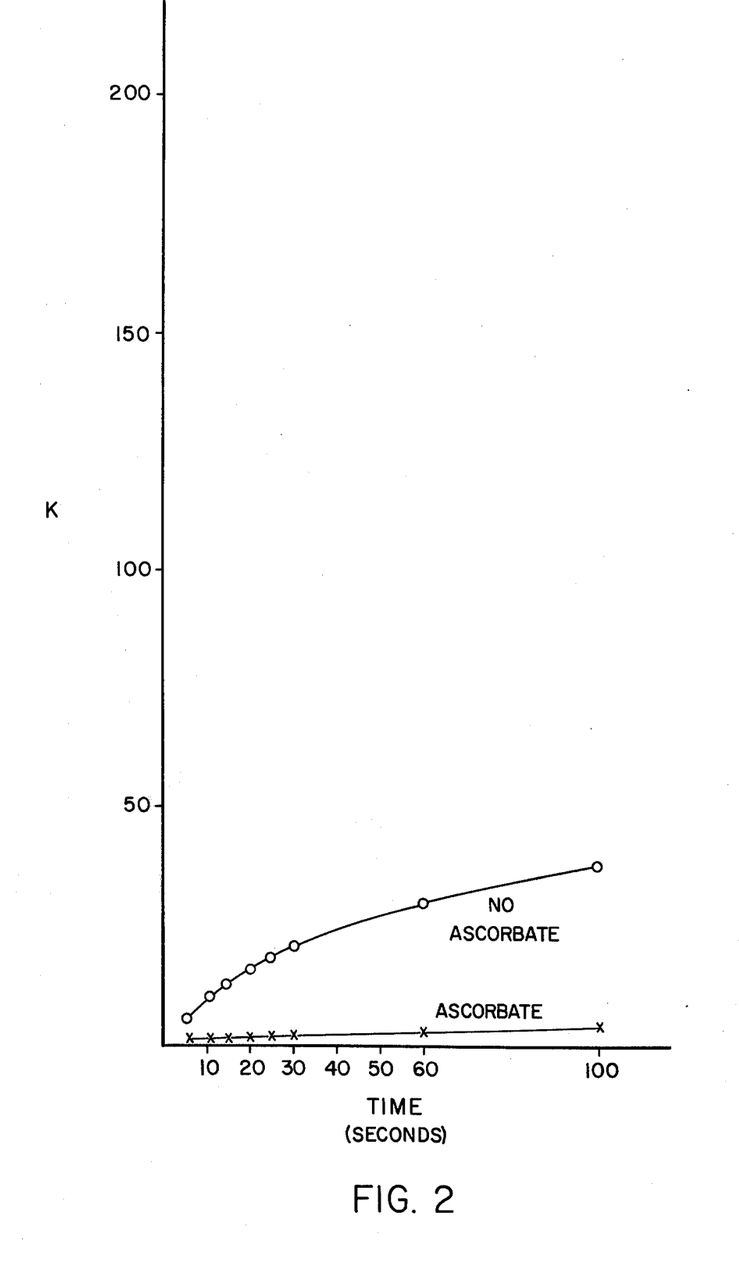
FIG. 2 is a graphical representation of the data reported in Example II for a glucose oxidase-peroxidase reagent test using MBTH/diethylaniline (DEA) as the indicator, obtained by plotting K vs. time.
Figure 3:
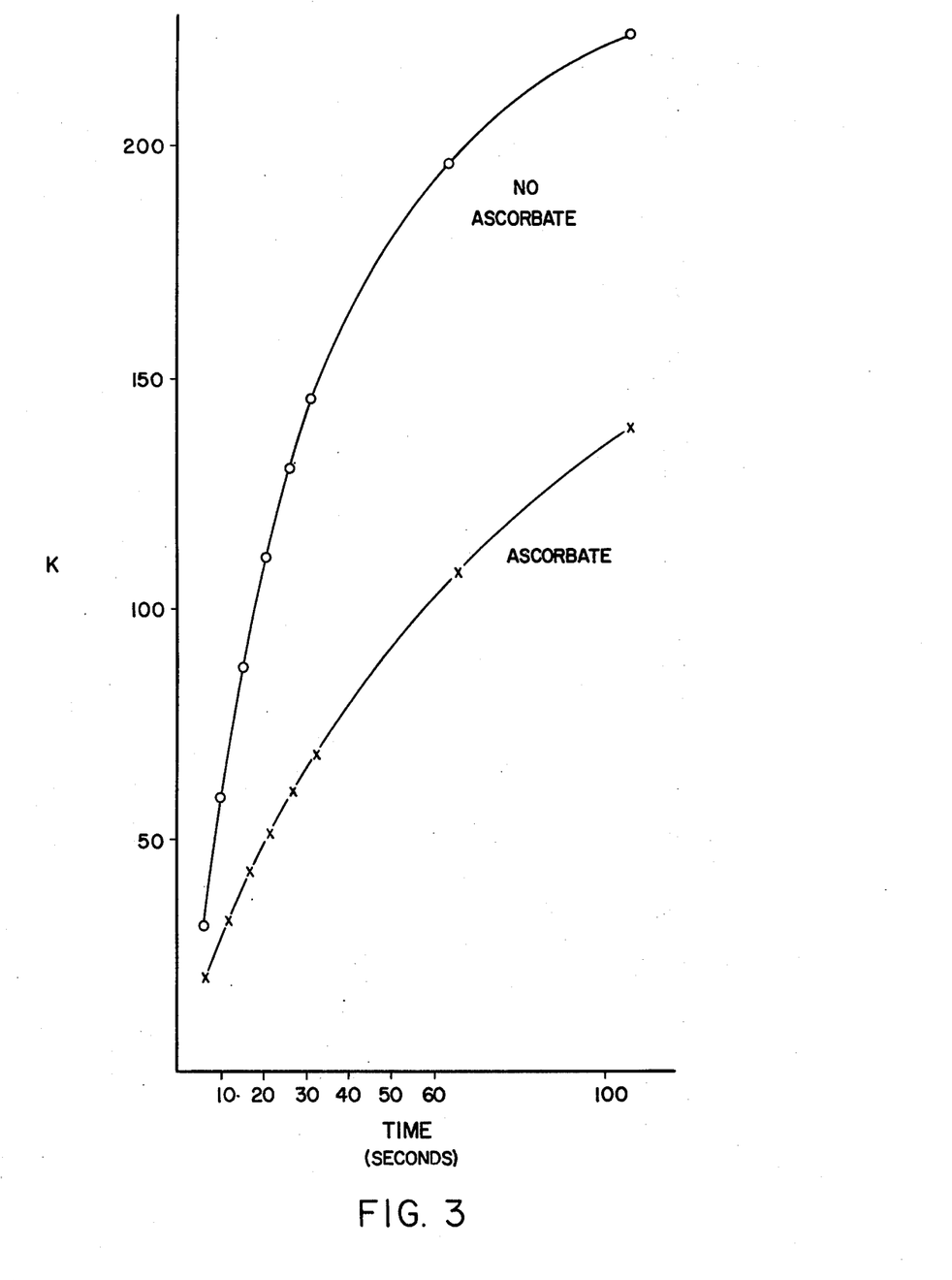
FIG. 3 is a graphical representation of the data reported in Example II for a glucose oxidase-peroxidase reagent test using MBTH/chromotropic acid (CTA) in accordance with the invention as the indicator, obtained by plotting K vs. time.

The results obtained at various times and their respective K values are graphically illustrated in FIG. 1 for o-tolidine, FIG. 2 for MBTH/DEA, and FIG. 3 for the MBTH/CTA device, prepared according to the invention.

These data clearly demonstrate that MBTH/chromotropic acid had an ascorbate resistance much superior to o-tolidine, and indeed is significantly (6 times) more ascorbate resistant than the prior art formulas based on MBTH/diethylaniline.

EXAMPLE III

Solutions prepared as set forth below with compositions according to the invention were compared with those of the prior art for the effect of pH and buffer variance in solutions with and without ascorbate.

Original test solutions at pH 5.0 were prepared in 0.311 M citrate buffer. Original test solutions at pH 7.0 were prepared in 0.093 M Tris [Tris(hydroxymethyl)aminomethane] combined with 0.093 M malonate. In each buffer system, test solutions were prepared to concentrations of 100 μM MBTH, 100 μM coupler, 333 μM $H_2O_2$, and 56.8 μM (1 mg/dl) ascorbic acid.

The above solutions were assayed in 3 ml standard glass or quartz cuvettes. In each case the reaction was allowed to proceed by injection of peroxidase to a concentration of 125 nanograms (ng)/ml. Changes in optical density (ΔOD) were recorded by a standard recording absorbance spectrophotometer with the results shown in Tables 3 and 4.

Table 3

| | Tris-Malonate Buffer (pH 7) | | |
|---|---|---|---|
| | | Rate of Reaction (ΔOD/min.) | |
| MBTH Coupler | Wave Length | No Ascorbate | Ascorbate |
| Chromotropic acid | 572 nm | 0.600 | 0.223 |

Table 3-continued

| | Tris-Malonate Buffer (pH 7) | | |
|---|---|---|---|
| | | Rate of Reaction (ΔOD/min.) | |
| MBTH Coupler | Wave Length | No Ascorbate | Ascorbate |
| N,N-dimethylaniline | — | No reaction | No reaction |
| 1-hydroxy-2-naphthalenesulfonic acid | 495 nm | 0.373 | 0.159 |
| 1-hydroxy-3-naphthalenesulfonic acid | 490 nm | 0.545 | 0.0977 |
| 1-hydroxy-5-naphthalenesulfonic acid | 495 nm | 0.493 | 0.0815 |

Table 4

| | Citric Acid Buffer (pH 5) | | |
|---|---|---|---|
| | | Rate of Reaction (ΔOD/min.) | |
| MBTH Coupler | Wave Length | No Ascorbate | Ascorbate |
| Chromotropic acid | 572 nm | 0.162 | 0.0065 |
| N,N-dimethylaniline | 570 nm | 0.189 | 0.0000 |
| 1-hydroxy-2-naphthalenesulfonic acid | 495 nm | 0.0891 | 0.0037 |
| 1-hydroxy-3-naphthalenesulfonic acid | 490 nm | 0.0992 | 0.0000 |
| 1-hydroxy-5-naphthalenesulfonic acid | 495 nm | 0.0822 | 0.0000 |

Figure 4:
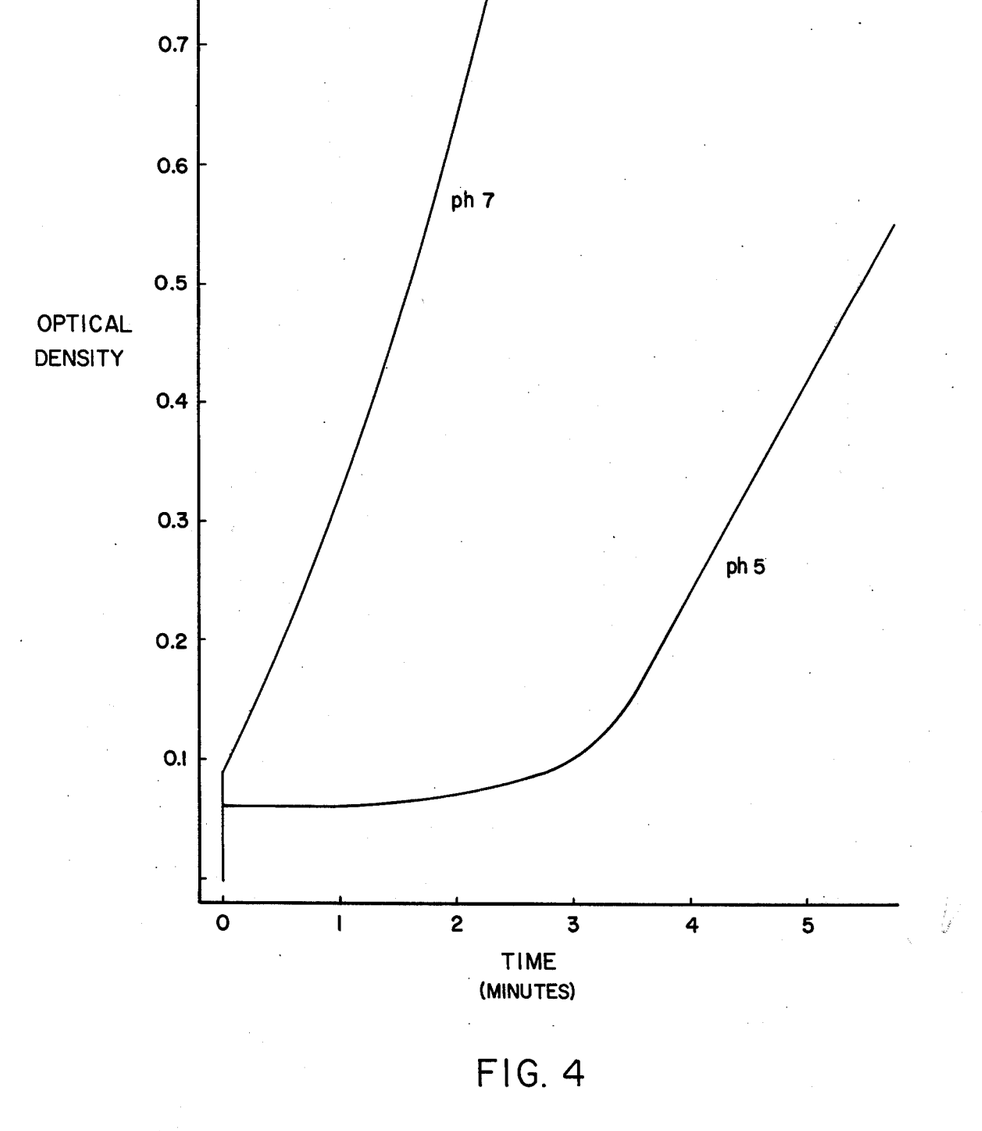
FIG. 4 is a graphical representation of the data reported in Example III for MBTH/CTA in accordance with the invention at different pH levels, obtained by plotting optical density (OD) vs. time.
Figure 5:
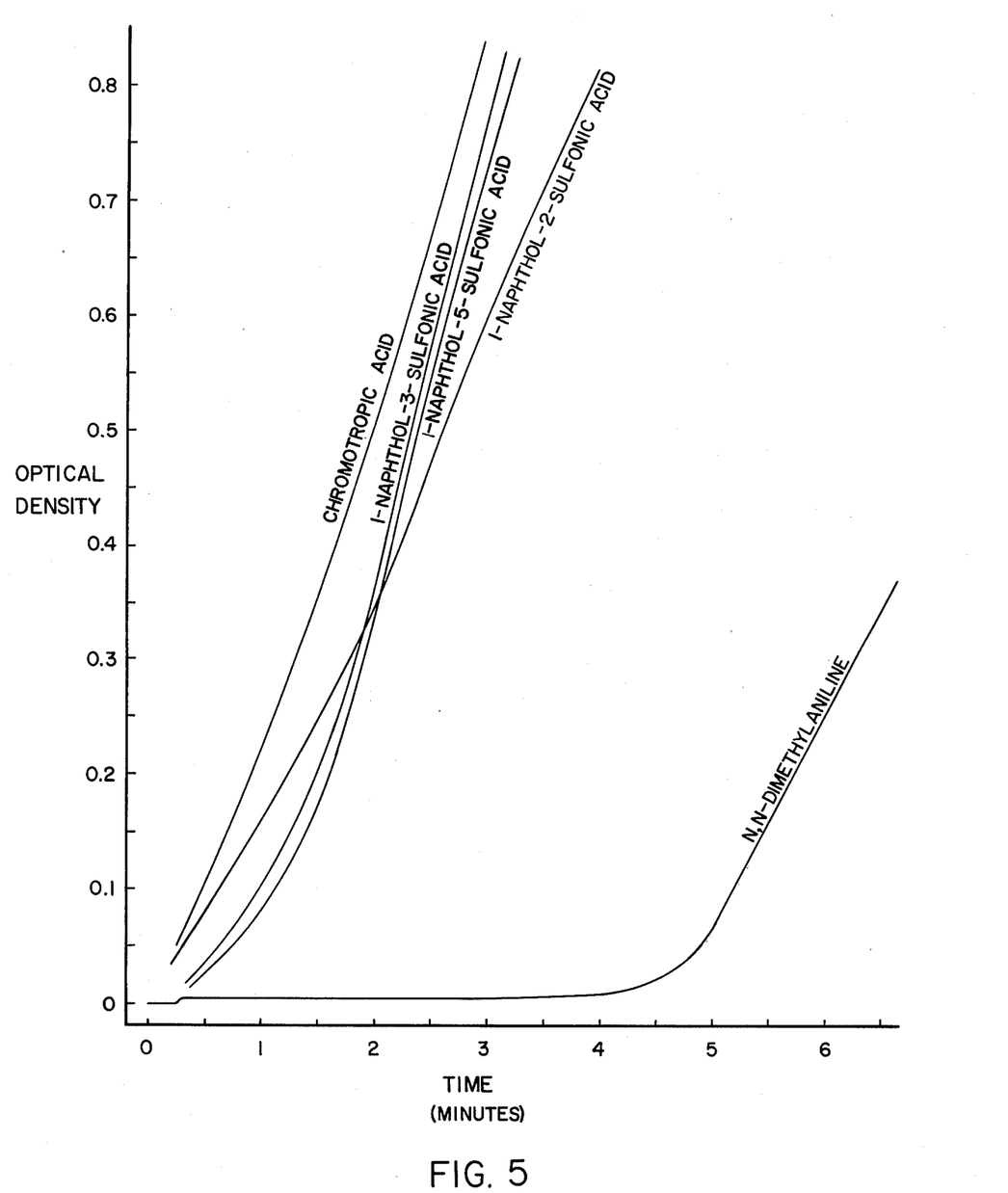
FIG. 5 is a graphical representation of the data reported in Example III for the various MBTH couplers in Tris-Malonate buffer (pH 7) with the exception that the dimethylaniline slope is that observed in citric acid buffer (pH 5).

The results observed in the Tris Malonate buffer system at pH 7 for each of the couplers according to the invention were much superior to the dimethylaniline. They were more reactive both in the presence and absence of ascorbate. The activity at about pH 7.0 in terms of color development (ΔOD) per minute was about 3-4 times that in citric acid at pH 5.0 without ascorbate and an even greater difference is seen with ascorbate. The results obtained at various times and their respective absorbance (optical density) values are graphically illustrated in FIG. 4 for MBTH/chromotropic acid in Tris Malonate (pH 7) and citric acid (pH 5) systems. A comparison of results obtained with the various couplers is graphically illustrated in FIG. 5 for the Tris Malonate (pH 7) system, with one notable exception. Since the prior art coupler, dimethylaniline, would not even react under these parameters, its curve is taken from the citric acid (pH 5) data.

Thus, unlike previous coupling systems, those of the present invention are optionally functional in a preferred physiological pH range, especially important in enzyme assays.

EXAMPLE IV

Devices prepared in the manner described below to incorporate compositions according to the invention were subjected to periods of elevated temperature in this example to examine their stability.

A buffer for use in the first impregnating solution was prepared by adding 19.8 g citric acid, 87.2 g sodium citrate, 66.8 g of the ethylenediamine tetraacetic acid (Versene ®, Dow Chemical Co.) to 935 ml $H_2O$, with stirring.

Four aliquots of a first impregnating solution were then prepared, each by combining 50 ml of the above-prepared buffer, 13 ml of 10% methyl vinyl ether-maleic anhydride copolymer (Gantrez), 10 ml of 5% PVP, and 0.15 g of peroxidase, and adding, respectively, glucose oxidase and water as shown in Table 5.

Table 5

| Formula | Glucose Oxidase | H$_2$O |
|---|---|---|
| 1 | 5 ml | 35 ml |
| 2 | 10 ml | 30 ml |
| 3 | 20 ml | 20 ml |
| 4 | 40 ml | 0 ml |

Four sheets of E&D paper were impregnated to saturation, each with one of the above-prepared formulas and dried at 90° C.

A second impregnating solution was prepared by dissolving 0.32 g chromotropic acid, 0.8 g. sodium lauryl sulfate and 2.4 g MBTH in a solvent of 160 ml methanol and 40 ml H$_2$O. The above-prepared sheets were then impregnated to saturation with this second solution, dried at 50° C. and cut to 2.5 mm × 2.5 mm to form devices according to the invention. The devices so prepared were fixed, by double-faced adhesive tape, to organo-plastic handles for convenience.

Half of these devices were subjected to dry heat of 60° C. for 3 days in a standard laboratory oven while the other half were maintained at room temperature (RT) to serve as controls. The devices, both heat-stressed and controls, were then tested by momentary immersion in urine samples having the concentrations of glucose shown in Table 6. The results observed are reported by comparison of the color observed in the control and heat-stressed devices. Color blocks of increasing intensity indicate various glucose concentrations and are assigned arbitrary numerical values (0–70) as follows:

| mg% | 0 | 50 | 100 | 250 | 500 | 1000 | 2000 | >2000 |
|---|---|---|---|---|---|---|---|---|
| Values | 0 | 10 | 20 | 30 | 40 | 50 | 60 | 70 |

The results for the heat-stressed devices are reported as comparative to those of the corresponding control.

Table 6

| | Formula No. | | | | | | | |
|---|---|---|---|---|---|---|---|---|
| Glucose | 1 | | 2 | | 3 | | 4 | |
| Mg% Value | RT | 60°C | RT | 60°C | RT | 60°C | RT | 60°C |
| 0 = 0 | 0 | 0 | 0 | 0 | 0 | 0 | 0 | 0 |
| 50 = 10 | 10 | 8 | 25 | 20 | 35 | 32 | 45 | 42 |
| 100 = 20 | 20 | 18 | 45 | 42 | 48 | 45 | 55 | 55 |
| 250 = 30 | 30 | 28 | 55 | 52 | 60 | 58 | 60 | 60 |
| 500 = 40 | 40 | 37 | 60 | 58 | 65 | 62 | 70 | 70 |
| 1000 = 50 | 50 | 45 | 65 | 62 | 70 | 70 | >70 | >70 |
| 2000 = 60 | 60 | 55 | 70 | 70 | 70 | 70 | >70 | >70 |

In comparing the stressed strips, formulation 4 proved the least affected. Even in formulation 1, the most affected, there is no substantial difference in the intensity of the color produced by the stressed and unstressed devices. Thus, no real loss of sensitivity is observed in any of the formulations.

Although the invention has been described with a certain degree of particularity, it is understood that the present disclosure has been made only by way of example and that numerous changes in the details may be resorted to without departing from the scope of the invention.

What is claimed is:

1. Test means for the determination of an oxidizing substance which comprises a hydrazone and hydroxynapthalenesulfonate selected from the group of 4,5-dihydroxy-2,7-napthalene-disulfonic acid and 1-hydroxy-2-napthalene-sulfonic acid.

2. The test means of claim 1 wherein said hydroxynapthalenesulfonate is 4,5-dihydroxy-2,7-napthalene-disulfonic acid.

3. The test means of claim 1 wherein said hydrazone is 3-methyl-2-benzothiazolinone hydrazone.

4. The test means of claim 2 wherein said hydrazone is 3-methyl-2-benzothiazolinone hydrazone.

5. A test device for the determination of an oxidizing substance which comprises a carrier matrix and, incorporated therewith, the test means of claim 1.

6. A test device for the determination of an oxidizing substance which comprises a carrier matrix and, incorporated therewith, the test means of claim 4.

7. The device of claim 5 wherein the carrier matrix is bibulous.

8. A test device for the determination of an oxidizing substance which comprises a tablet incorporated with the test means of claim 1.

9. A process for the preparation of a device for the determination of oxidizing substances which comprises incorporating a carrier matrix with the test means of claim 1.

10. The process of claim 9 wherein said incorporating is impregnating with a solution of said test means, followed by drying.

11. A process for determination of an oxidizing substance in a liquid sample which comprises contacting said sample with the test means of claim 1 and observing any resultant color formed.

12. A process for determination of an oxidizing substance in a liquid sample which comprises contacting said sample with the test device of claim 5 and observing any resultant color formed thereon.

13. In a test system for the determination of a constituent in a sample, having means responsive to the presence of said constituent in said sample to produce at least one oxidizing substance and having a composition for determining said at least one oxidizing substance, the improvement wherein said composition comprises a hydrazone and a hydroxynapthalenesulfonate selected from the group of 4,5-dihydroxy-2,7-napthalene disulfonic acid and 1-hydroxy-2-napthalene sulfonic acid.

14. The test system of claim 13 wherein said hydroxynapthalenesulfonate is 4,5-dihydroxy-2,7-napthalene-disulfonic acid.

15. The test system of claim 13 wherein said hydrazone is 3-methyl-2-benzothiazolinone hydrazone.

16. The test system of claim 14 wherein said hydrazone is 3-methyl-2-benzothiazolinone hydrazone.

17. A test device which comprises a carrier matrix and, incorporated therewith, the test system of claim 13.

18. A test device which comprises a carrier matrix and, incorporated therewith, the test system of claim 16.

19. The device of claim 17 wherein the carrier matrix is bibulous.

20. A test device which comprises a tablet incorporated with the test system of claim 13.

21. A process for the preparation of a test device which comprises incorporating a carrier matrix with the test system of claim 13.

22. The process of claim 21 wherein said incorporating is impregnating with a solution of said test system, followed by drying.

23. A process for determination of a constituent in a liquid sample which comprises contacting said sample with the test system of claim 13 and observing any resultant color formed.

24. A process for determination of a constituent in a liquid sample which comprises contacting said sample with the test device of claim 17 and observing any resultant color formed.

* * * * *